US008512387B2

(12) United States Patent
Fishel

(10) Patent No.: US 8,512,387 B2
(45) Date of Patent: Aug. 20, 2013

(54) ESOPHAGEAL COOLING SYSTEM FOR ABLATION PROCEDURES ASSOCIATED WITH CARDIAC ARRHYTHMIAS

(76) Inventor: Robert S. Fishel, Delray Beach, FL (US)

( * ) Notice: Subject to any disclaimer, the term of this patent is extended or adjusted under 35 U.S.C. 154(b) by 1657 days.

(21) Appl. No.: 11/851,465

(22) Filed: Sep. 7, 2007

(65) Prior Publication Data

US 2009/0069875 A1   Mar. 12, 2009

(51) Int. Cl.
*A61F 7/00* (2006.01)
(52) U.S. Cl.
USPC .............................. 607/113; 607/5; 128/898
(58) Field of Classification Search
USPC .................. 607/5, 105, 113, 104; 606/20–23, 606/34; 604/27, 113; 128/898
See application file for complete search history.

(56) References Cited

U.S. PATENT DOCUMENTS

| 3,951,136 | A | 4/1976 | Wall |
| 4,569,801 | A | 2/1986 | Molloy et al. |
| 4,641,649 | A | 2/1987 | Walinsky et al. |
| 4,673,563 | A | 6/1987 | Berne et al. |
| 4,898,591 | A | 2/1990 | Jang et al. |
| 5,104,393 | A | 4/1992 | Isner et al. |
| 5,398,692 | A | 3/1995 | Hickey |
| 5,487,385 | A | 1/1996 | Avitall |
| 5,570,671 | A | 11/1996 | Hickey |
| 5,575,766 | A | 11/1996 | Swartz et al. |
| 5,582,609 | A | 12/1996 | Swanson et al. |
| 5,617,854 | A | 4/1997 | Munsif |
| 5,928,145 | A | 7/1999 | Ocali et al. |
| 6,031,375 | A | 2/2000 | Atalar et al. |
| 6,383,181 | B1 * | 5/2002 | Johnston et al. ............... 606/24 |
| 6,508,777 | B1 * | 1/2003 | Macoviak et al. .......... 604/4.01 |
| 6,607,517 | B1 | 8/2003 | Dae et al. |
| 6,811,562 | B1 | 11/2004 | Pless |

(Continued)

FOREIGN PATENT DOCUMENTS

| WO | WO9320767 | 10/1993 |
| WO | WO9632897 | 10/1996 |

OTHER PUBLICATIONS

J. Cox et al, "The surgical treatment of atrial fibrillation. I. Summary of the current concepts of the mechanisms of atrial flutter and atrial fibrillation", J. Thorac Cardiovasc Surg., 101(3):402-405 (Mar. 1991) (Abstract only).

(Continued)

*Primary Examiner* — Cris L Rodriguez
*Assistant Examiner* — Matthew Seward
(74) *Attorney, Agent, or Firm* — McHale & Slavin, P.A.

(57) ABSTRACT

The invention involves a system and method for an esophageal cooling system suitable for use during surgical procedures associated with the left atrium of the heart and most particularly ablation procedures associated with atrial fibrillation. The esophageal cooling system is suitable for use irrespective of whether the ablation procedure is intraoperative or catheter based. The system includes an esophageal catheter constructed and arranged to fit within the patients esophagus. Suitably located along the esophageal catheter is a phoximal balloon for occluding an upper portion of the esophagus. The phoximal balloon includes a coolant lumen for transferring temperature controlled liquid to the area where the esophagus may be in contact with the atrium of the heart. The liquid is expelled through a nozzle which directs the liquid to the inner surface of the esophagus. A suction lumen also extends through the phoximal balloon to evacuate the used coolant from the lower portion of the esophagus or gastrum of the patient.

17 Claims, 3 Drawing Sheets

(56) References Cited

U.S. PATENT DOCUMENTS

| | | | |
|---|---|---|---|
| 6,869,431 B2* | 3/2005 | Maguire et al. | 606/41 |
| 7,077,825 B1* | 7/2006 | Stull | 604/113 |
| 7,175,649 B2 | 2/2007 | Machold et al. | |
| 7,189,254 B2 | 3/2007 | Magers | |
| 2002/0095197 A1 | 7/2002 | Lardo et al. | |
| 2005/0065584 A1* | 3/2005 | Schiff et al. | 607/105 |
| 2006/0142827 A1* | 6/2006 | Willard et al. | 607/105 |
| 2007/0055328 A1* | 3/2007 | Mayse et al. | 607/105 |

OTHER PUBLICATIONS

J. Cox, "The surgical treatment of atrial fibrillation. IV. Surgical Technique", J. Thorac Cardiovasc Surg., 101 (4):584-592 (Apr. 1991) (Abstract only).

T. Sueda et al, "Simple left atrial procedure for chronic atrial fibrillation associated with mitral valve disease", Ann Thorac Surg., 62(6):1796-1800 (Dec. 1996) (Abstract only).

B. Avitall et al, "Physics and engineering of transcatheter cardiac tissue ablation", J Am Coll Cardiol., 22:921-932 (1993) (Abstract only).

M. Haissaguerre et al, "Right and left atrial radiofrequency catheter therapy of paroxysmal atrial fibrillation", J. Cardiovasc Electrophysiol., 7(12):1132-1144 (Dec. 1996) (Abstract only).

D. Fram et al, "Feasibility of radiofrequency powered, thermal balloon ablation of atrioventricular bypass tracts via the coronary sinus: in vivo canine studies", PACE, 18(8):1518-1530 (Jun. 2006) (Abstract only).

C. Schuger et al, "Long-term effects of percutaneous laser balloon ablation from the canine coronary sinus", Circulation, 86:947-954 (1992) (Abstract only).

L. Mcmath et al, "Percutaneous laser balloon coagulation of accessory pathways", Proc. SPIE, 1425:165 (1991) (Abstract only).

P. Jais et al, "A focal source of atrial fibrillation treated by discrete radiofrequency ablation", Circulation, 95:572-576 (1997) (Abstract only).

T. Hiraki et al, "Radiofrequency ablation of metastatic mediastinal lymph nodes during cooling and temperature monitoring of the tracheal mucosa to prevent thermal tracheal damage: initial experience", Radiology, 237:1068-1074 (2005).

C. Perzanowski et al, "Real-time monitoring of luminal esophageal temperature during left atrial radiofrequency catheter ablation for atrial fibrillation: observations about esophageal heating during ablation at the pulmonary vein ostia and posterior left atrium", J. Cardiovasc Electrophysiol., 17:166-170 (Feb. 2006).

F. Hornero et al, "Esophageal temperature during radiofrequency-catheter ablation of left atrium: a three-dimensional computer modeling study", J. Cardiovasc Electrophysiol., 17:405-410 (Apr. 2006).

E. Berjano et al, "A cooled intraesophageal balloon to prevent thermal injury during endocardial surgical radiofrequency ablation of the left atrium: a finite element study", Phys. Med. Biol., 50:N269-N279 (2005).

T. Tsuchiya et al, "Atrial fibrillation ablation with esophageal cooling with a cooled water-irrigated intraesophageal balloon: a pilot study", J. Cardiovasc Electrophysiol, 18:145-150 (Feb. 2007).

\* cited by examiner

ESOPHAGEAL COOLING SYSTEM FOR ABLATION PROCEDURES ASSOCIATED WITH CARDIAC ARRHYTHMIAS

FIELD OF INVENTION

The present invention generally relates to Esophageal Cooling Systems and more particularly to an Esophageal Cooling System for Ablation Procedures Associated with Cardiac Arrhythmias.

BACKGROUND INFORMATION

Cardiac arrhythmias, and atrial fibrillation in particular, are common, dangerous medical ailments, particularly in the aging population. In patients with normal sinus rhythm, the heart, which is made up of atrial, ventricular, and excitatory conduction tissue, is electrically excited to beat in a synchronous, patterned fashion. In patients with cardiac arrhythmia, regions of cardiac tissue do not follow the synchronous beating cycle associated with the normally conductive tissue in patients with sinus rhythm. Instead, the abnormal regions of cardiac tissue aberrantly conduct to adjacent tissue, thereby disrupting the cardiac cycle into an asynchronous cardiac rhythm. Such abnormal conduction generally occurs at various, specific regions of the heart, for example: in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmia, may be of a multiwavelet re-entrant type, characterized by multiple asynchronous loops of electrical impulses that are scattered about the atrial chamber. These arrhythmias are often self propagating. Cardiac arrhythmias may also have a focal origin, such as when an isolated region of tissue in an atrium fires autonomously in a rapid, repetitive fashion. Cardiac arrhythmias, including atrial fibrillation, may be detected using the global technique of an electrocardiogram (EKG). More sensitive procedures of mapping the specific conduction along the cardiac chambers have also been disclosed, such as for example in U.S. Pat. No. 4,641,649 to Walinsky et al and WO 96/32897 to Desai.

A variety of clinical conditions may result from the irregular cardiac function and resulting hemodynamic abnormalities associated with atrial fibrillation, including stroke, heart failure, and other thromboembolic events. Atrial fibrillation is believed to be a significant cause of cerebral stroke; the abnormal hemodynamics in the left atrium caused by the fibrillatory wall motion precipitate the formation of thrombus within the atrial chamber. A thromboembolism is ultimately thrown off into the left ventricle, which then pumps the embolism into the cerebral circulation causing a stroke. For these reasons, there are a number of procedures for treating atrial arrhythmias.

Conventional Atrial Arrhythmia Treatments

There are several pharmacological approaches intended to remedy or otherwise treat atrial arrhythmias. See for example, U.S. Pat. No. 4,673,563, to Beme et al; U.S. Pat. No. 4,569,801, to Molloy et al; and Hindricks, et al in "Current Management of Arrhythmias" (1991). However, such pharmacological solutions are not always effective and may in some cases result in proarrhythmia and long term inefficacy.

Several surgical approaches have been developed to treat atrial fibrillation. One example is known as the "maze procedure," as is disclosed by Cox, J. L. et al in "The surgical treatment of atrial fibrillation. I. Summary" Thoracic and Cardiovascular Surgery 101(3), pp. 402-405 (1991); and also by Cox, J. L. in "The surgical treatment of atrial fibrillation. IV. Surgical Technique", Thoracic and Cardiovascular Surgery 101(4), pp. 584-592 (1991). In general, the "maze" procedure is designed to relieve atrial arrhythmia by restoring effective atrial systole and sinus node control via a specific pattern of incisions in the tissue wall. Early on, the "maze" procedure included surgical incisions in both the right and the left atrial chambers. However, more recent reports predict that the surgical "maze" procedure may be effective when performed only in the left atrium. See, Sueda et al, "Simple Left Atrial Procedure for Chronic Atrial Fibrillation Associated With Mitral Valve Disease" (1996).

The "maze procedure" as surgically performed in the left atrium generally includes forming vertical incisions from the two superior pulmonary veins and terminating in the region of the mitral valve annulus, traversing the inferior pulmonary veins en route. An additional horizontal incision also connects the superior ends of the two vertical incisions. The atrial wall region bordered by the pulmonary vein ostia is therefore isolated from the other atrial tissue. In this way, the mechanical sectioning of atrial tissue eliminates the precipitating conduction to the atrial arrhythmia by creating conduction blocks within the aberrant electrical conduction pathways.

Although the "maze" procedure is generally effective, it is a highly invasive procedure. Nevertheless, the procedures have provided a guiding principle for alleviating arrhythmia: the mechanical isolation of faulty cardiac tissue often prevents atrial arrhythmia, and particularly atrial fibrillation caused by perpetually wandering reentrant wavelets or focal regions of arrhythmogenic conduction.

Modern Catheter Treatments for Atrial Arrhythmia

Success with surgical interventions through atrial segmentation, particularly with regard to the surgical "maze" procedure just described, has caused others to develop less invasive catheter-based approaches to treat atrial fibrillation through cardiac tissue ablation. Examples of such catheter-based devices and treatment methods have generally targeted atrial segmentation with ablation catheter devices and methods adapted to form linear or curvilinear lesions in the wall tissue which defines the atrial chambers, such as are disclosed in the following: U.S. Pat. No. 5,617,854, to Munsif; U.S. Pat. No. 4,898,591, to Jang et al; U.S. Pat. No. 5,487,385, to Avitall; and U.S. Pat. No. 5,582,609 to Swanson.

Addition al examples of catheter-based tissue ablation in performing less-invasive cardiac chamber segmentation procedures are also disclosed in the following articles: "Physics and Engineering of Transcatheter Tissue Ablation", Avitall et al., Journal of American College of Cardiology, Volume 22, No. 3:921-932 (1993); and "Right and Left Atrial Radiofrequency Catheter Therapy of Paroxysmal Atrial Fibrillation," Haissaguerre, et al., Journal of Cardiovascular Electrophysiology 7(12), pp. 1132-1144 (1996).

Furthermore, various energy delivery modalities (microwave, laser, and more commonly, RF) is used to create conduction blocks (atrial wall lesions) along the cardiac tissue wall. See, WO 93/120767, to Stem et al; U.S. Pat. No. 5,104,393, to Isner et al; and U.S. Pat. No. 5,575,766, to Swartz et al.

Additionally, ablation catheter devices and methods have also been used to ablate arrhythmogenic tissue of the left-sided accessory pathways, such as those associated with the Wolff-Parkinson-White syndrome, through the wall of an adjacent region along the coronary sinus.

For example, Fram et al, in "Feasibility of RF Powered Thermal Balloon Ablation of Atrioventricular Bypass Tracts via the Coronary Sinus: In vivo Canine Studies," PACE, Vol. 18, pp. 1518-1530 (1995), discloses attempted thermal ablation of left-sided accessory pathways in dogs using a balloon which is heated with bipolar radiofrequency electrodes positioned within the balloon. Fram et al suggests that the lesion depth of some population groups may be sufficient to treat patients with Wolff-Parkinson-White syndrome.

Additional examples of cardiac tissue ablation from the region of the coronary sinus for the purpose of treating particular types of cardiac arrhythmias are disclosed in: "Long-term effects of percutaneous laser balloon ablation from the canine coronary sinus", Schuger C D et al., Circulation (1992) 86:947-954; and "Percutaneous laser balloon coagulation of accessory pathways", McMath L P et al., Diagn. Ther. Cardiovasc. Interven. 1991; 1425:165-171.

Focal Arrhythmias Originating from Pulmonary Veins

Atrial fibrillation may be focal in nature, caused by the rapid and repetitive firing of an isolated center within the atrial cardiac muscle tissue. These foci, defined by regions exhibiting a concentric pattern of electrical activation, may act either to trigger atrial fibrillation or to sustain the fibrillation. Some studies have suggested that focal arrhythmia often originates from a tissue region along the pulmonary veins of the left atrium, and even more particularly in the superior pulmonary veins.

Less-invasive percutaneous catheter ablation techniques have been disclosed which use end-electrode catheter designs with the intention of ablating and thereby treating focal arrhythmias in the pulmonary veins. These ablation procedures are typically characterized by the incremental application of electrical energy to the tissue to form focal lesions designed to interrupt the inappropriate conduction pathways.

One example of a focal ablation method intended to destroy and thereby treat focal arrhythmia originating from a pulmonary vein is disclosed by Haissaguerre et al, "Right and Left Atrial Radiofrequency Catheter Therapy of Paroxysmal Atrial Fibrillation," Journal of Cardiovascular Electrophysiology 7(12), pp. 1132-1144 (1996). Haissaguerre et al discloses radiofrequency catheter ablation of drug-refractory paroxysmal atrial fibrillation using linear atrial lesions complemented by focal ablation targeted at arrhythmogenic foci. The site of the arrhythmogenic foci were generally located just inside the superior pulmonary vein.

In another focal ablation example, Jais et al. in "A focal source of atrial fibrillation treated by discrete radiofrequency ablation" Circulation 95:572-576 (1997) discusses the use of an RF ablative technique to patients with paroxysmal arrhythmias originating from focal sources variously in both the right and left atria.

Unfortunately, an atrioesophageal fistula is an uncommon but devastating and often fatal complication of atrial fibrillation ablation irrespective of whether an intraoperative or catheter based radiofrequency ablation is performed, and may result in an air embolus, sepsis, endocarditis, and/or gastrointestinal exsanguinations. In addition to this complication, other serious esophageal injuries involving acute pyloric spasms and gastric hypomotility have been reported. Those complications are considered to be due to the thermal injury that occurs during the delivery of RF energy to the posterior left atrial wall between the left and right pulmonary veins.

Although attention has been paid to avoid those serious complications, which may include reduction of the amount of RF energy delivered when ablating the left atrial posterior wall, monitoring the esophagus temperature, and moving the left atrial posterior line to the roof in order to avoid the left atrium posterior wall that may be in contact with the esophagus, there remains a need in the art for methods and devices to avoid such serious complications.

SUMMARY OF THE INVENTION

Thus, the present invention overcomes the disadvantages of the prior art, described above, by providing an esophageal cooling system suitable for use during surgical procedures associated with the left atrium of the heart and most particularly ablation procedures associated with atrial fibrillation. The esophageal cooling system is suitable for use irrespective of whether the ablation procedure is intraoperative or catheter based. The system includes a plurality of reusable and/or disposable components suitable for use with surgical procedures. One such component is an esophageal catheter constructed and arranged to fit within the patients esophagus. Suitably located along the esophageal catheter is a phoximal balloon for occluding an upper portion of the esophagus. The phoximal balloon includes a coolant lumen for transferring temperature controlled liquid to the area where the esophagus may be in contact with the atrium of the heart. The liquid is expelled through a nozzle which directs the liquid to the inner wall of the esophagus. A suction lumen also extends through the phoximal balloon to evacuate the used coolant from the lower portion of the esophagus or gastrum of the patient. The liquid may be disposed of after one cycle through the esophageal cooling system or alternatively may be recycled through a coolant tank having suitable pumps and/or heat exchangers for maintaining the liquid at a predetermined temperature.

Accordingly, it is an objective of the present invention to provide an Esophageal Cooling System for Ablation Procedures Associated with the Left Atrium.

It is a further objective of the present invention to provide a catheter which prevents damage to the esophagus during an ablation procedure.

It is yet a further objective of the present invention to provide an Esophageal Cooling System catheter which directs temperature controlled fluid against the inner surface of the esophagus during ablation procedures.

It is another objective of the instant invention to provide an Esophageal Cooling System catheter which includes a vacuum system for evacuation of fluid utilized for cooling of the esophageal wall.

It is still another objective of the instant invention to provide an Esophageal Cooling System catheter which includes temperature sensors for controlling the temperature of the water expelled against the esophageal wall.

It is still yet another objective of the instant invention to provide an Esophageal Cooling System catheter which includes temperature sensors for controlling the volume of the water expelled against the esophageal wall.

It is still a further objective of the instant invention to provide an Esophageal Cooling System which includes an electronic controller suitable for receiving feedback from the esophageal catheter and capable of making changes if necessary to the operating parameters of the system.

Still yet a further objective of the instant invention to provide an Esophageal Cooling System which is capable of manual operation, automatic operation or a combination of manual and automatic operation.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE PREFERRED EMBODIMENTS

Figure 1:
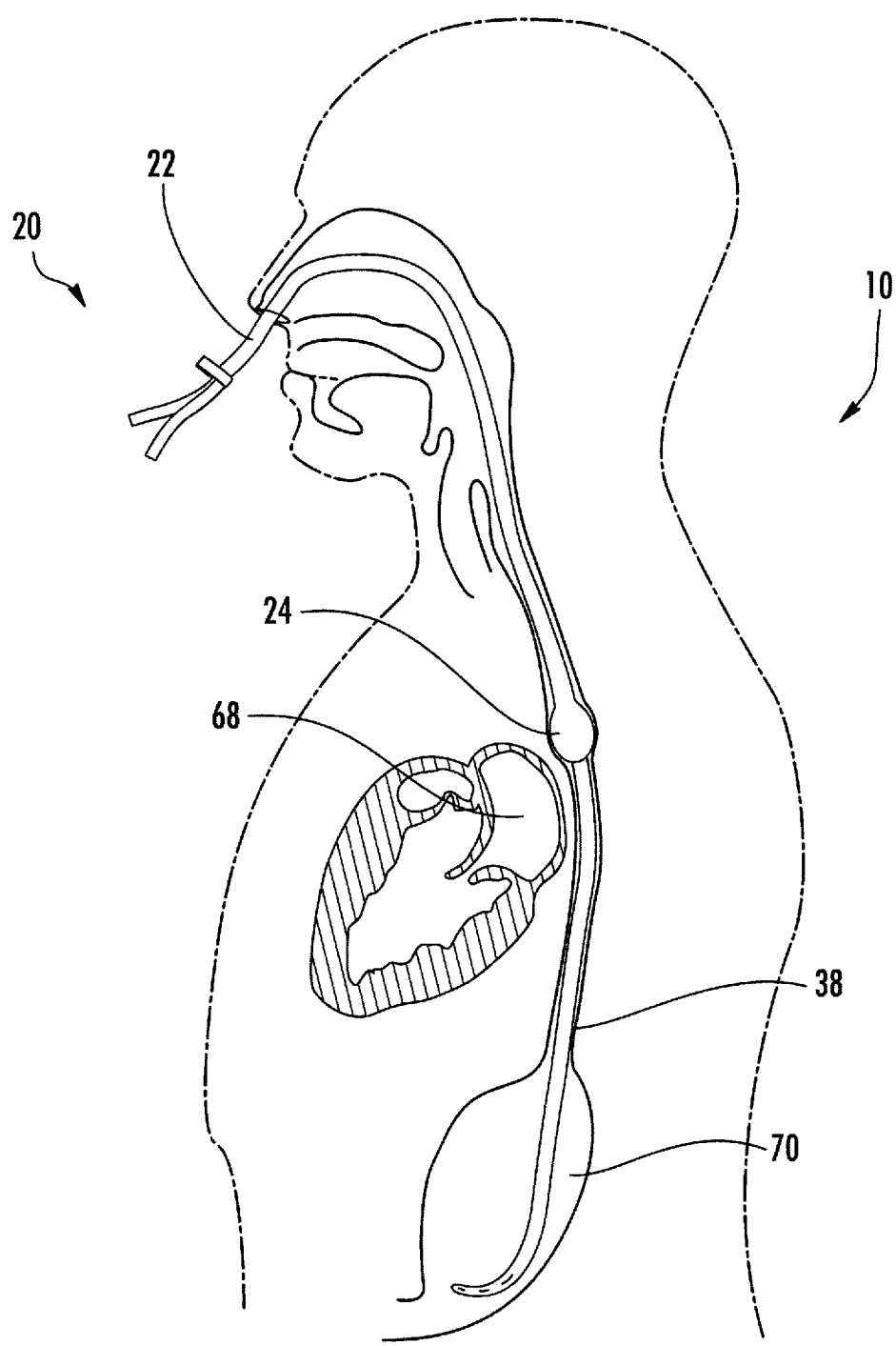
FIG. 1 is a side view of one embodiment of the instant invention, illustrating placement of the esophageal catheter.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiments illustrated.

Figure 2:
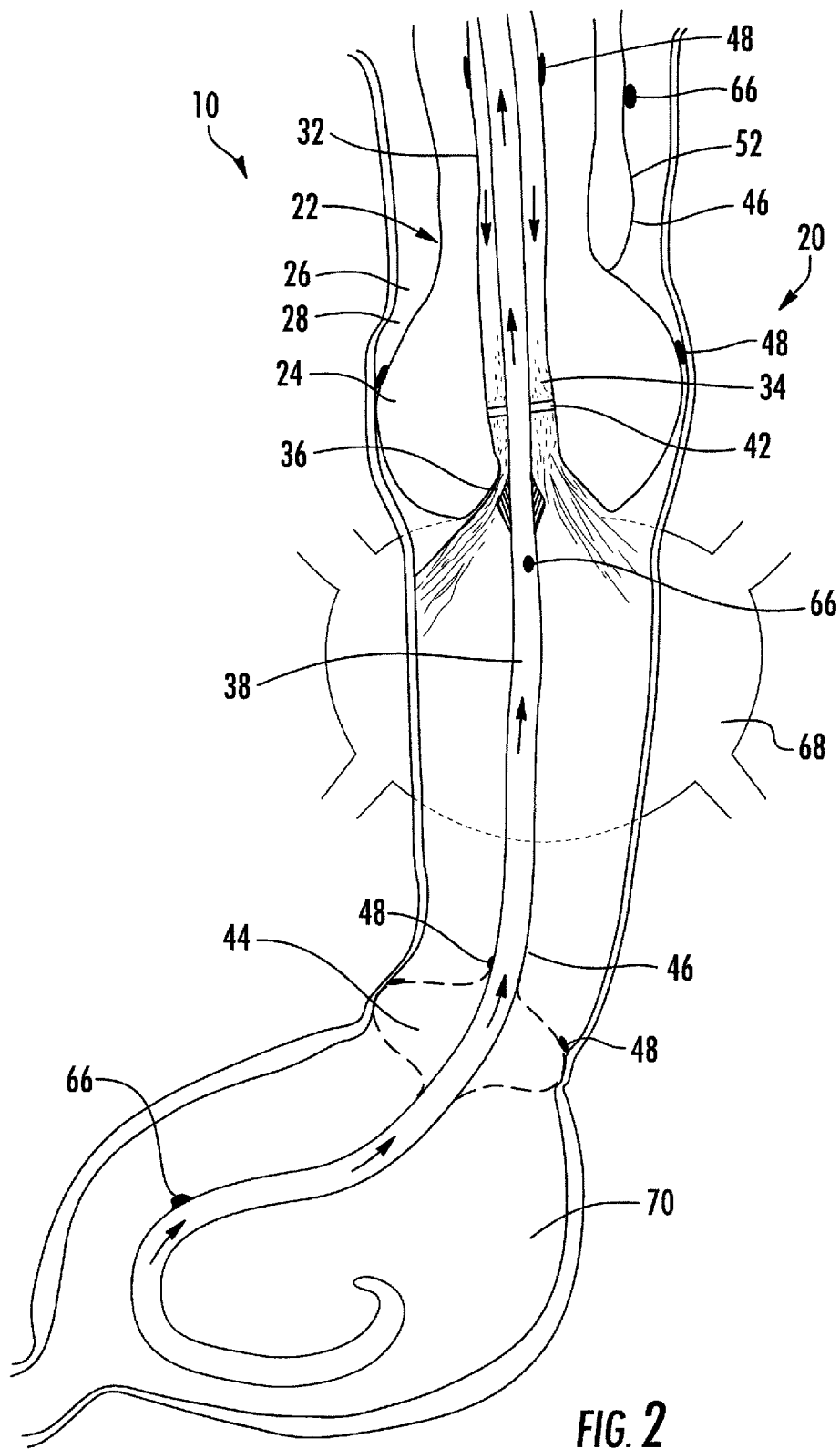
FIG. 2 is a partial posterior section view of one embodiment of the instant invention, illustrating location and operation of the device with respect to the left atrium.
Figure 3:
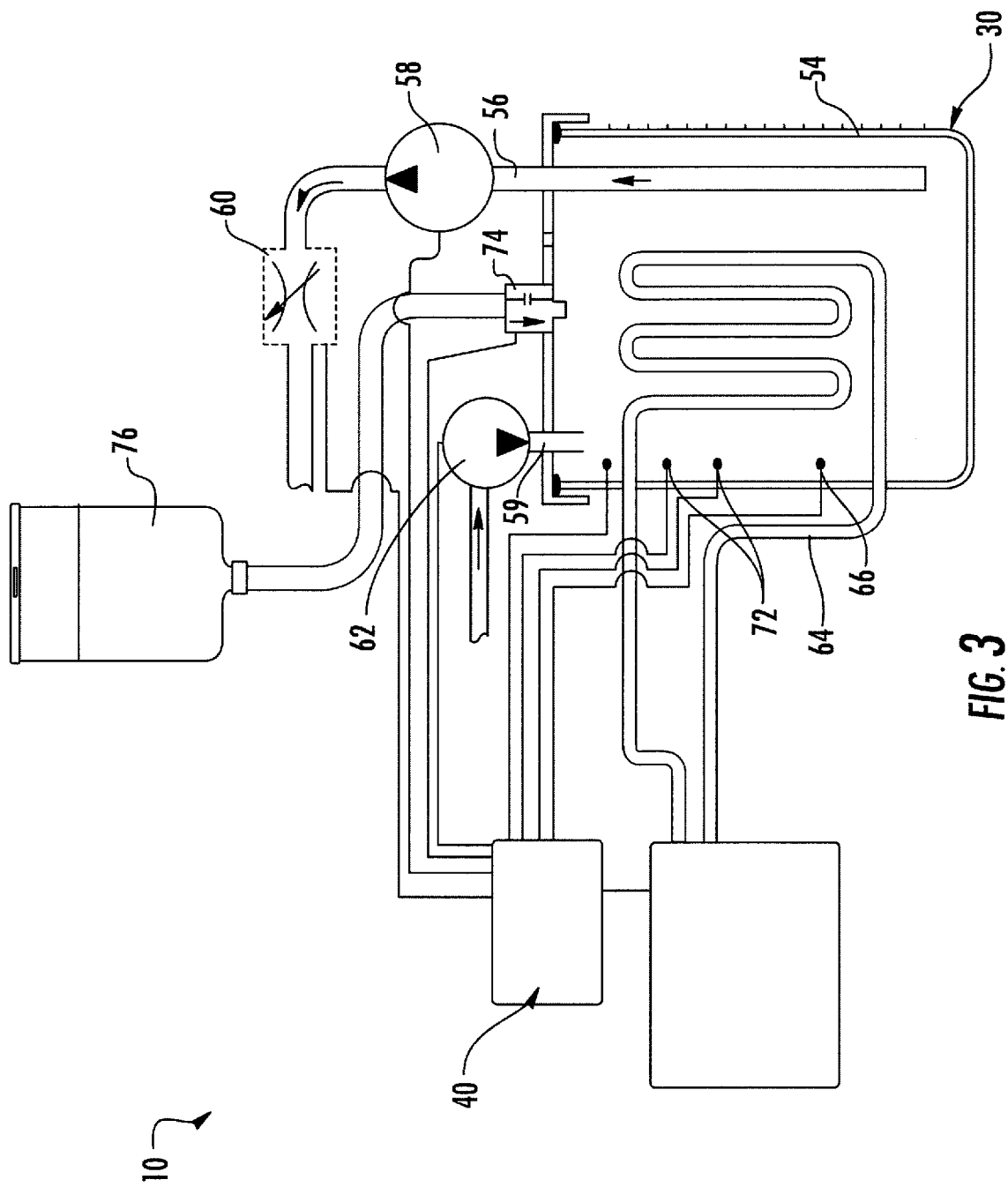
FIG. 3 is a schematic view of one embodiment of the coolant tank and controller of the instant invention.

Referring generally to FIGS. 1-3, an esophageal cooling system 10 particularly suited for ablation procedures associated with the left atrium is illustrated. The system generally includes an esophageal catheter 20 for placement within the esophagus of a patient, a cooling tank 30 and a controller 40 which are both located remote from the patient.

The esophageal catheter includes a phoximal balloon 24 constructed and arranged for occluding an upper portion 26 of an esophagus lumen 28. The phoximal balloon 24 includes a coolant lumen 32 therethrough for transfer of a liquid coolant 34. The coolant lumen terminates in a nozzle 36. The nozzle is constructed and arranged to direct the liquid coolant against the inner surface of the esophageal lumen. In a most preferred embodiment, the nozzle causes a frusta-conical shaped flow of the liquid coolant which is directed completely around the inner surface of the esophageal lumen. However, it should be noted that other types of nozzles, suitable for directing coolant against the inner surface of the esophagus, may be utilized without departing from the scope of the invention. A suction lumen 38 extends through the phoximal balloon 24 as well as the coolant lumen for evacuation of the liquid coolant after it is expelled against the inner surface of the esophagus. In a most preferred embodiment at least one stand-off 42 is constructed and arranged to extend between the suction lumen 38 and the coolant lumen 32 for locating and supporting the suction lumen within the central portion of the coolant lumen. Marker bands 48 which include a radio-opaque material such as gold or platinum may be utilized for locating various parts of the lumens or balloons by means of fluoroscopy while the catheter is in the body of the patient. All of the lumens and balloons are preferably constructed of a bio-compatible material and may include various coatings which reduce friction for insertion or aid in bio-compatibility. All of the components which contact the cooling fluid are preferably compatible with saline fluid as well as radio-opaque oral contrast agents such as gastographin and the like.

In one embodiment, the suction lumen 38 includes a second balloon 44 for occluding the esophagus at a position above the stomach. When the second balloon is utilized the suction lumen is provided with at least one suction port 46 positioned above the second balloon for transfer of liquid cooling fluid to the inside of the suction lumen 38 for evacuation thereof.

In another embodiment, the esophageal cooling system may include a second suction lumen 52, positioned above the phoximal balloon 24 for removing accumulated liquids above the phoximal balloon. The second suction lumen is also provided with at least one suction port 46 for transfer of fluid to the inner portion of the lumen for evacuation thereof.

Referring to FIG. 3, the esophageal cooling system includes a coolant tank 54 for containing the liquid coolant. The coolant tank is generally provided with an outlet aperture 56 in fluid communication with the coolant lumen 32 and an inlet aperture 59 in fluid communication with the suction lumen 38. A coolant pump 58 is utilized for transferring the cooling fluid from the tank 54 through a flow control 60 as well as the coolant lumen 32. The flow control may be manual and/or automatic, is used to allow volumetric control of the fluid passing through the coolant lumen. A vacuum pump 62 is also provided for transferring coolant fluid from the suction lumen 38 to the coolant tank 54. In this manner cooling fluid may be recycled through the system numerous times until the ablation procedure is completed. Alternatively, the fluid may be passed through the coolant lumen and returned to a drain, whereby the cooling fluid is cycled through the system only once.

Still referring to FIG. 3, the general use of a controlled system is illustrated. In this embodiment, the controller 40 is constructed and arranged to control at least one parameter of the system which may include, but should not be limited to, cooling fluid flow, cooling fluid temperature, vacuum operation, vacuum pressure, cooling fluid level within the coolant tank. The controller preferably includes a suitable processor and memory means to allow user pre-sets of the parameters that are desired to be controlled. The controller utilizes electrical communication with the various sensors embedded within the system for monitoring the parameters and adjusting the system accordingly. In one embodiment, the coolant lumen receives fluid regulated within the tank 54 by a heat-exchanger unit 64 which controls the temperature of the cooling fluid. The heat exchanger is preferably in electrical communication with the controller 40 which allows the temperature of the fluid to be manually or automatically adjusted to a desired temperature. The controller 40 receives signals from one or more sensors 66 which may be used to adjust the temperature of the fluid flowing through the esophageal cooling system. The temperature sensors illustrated are preferably thermistors, however other means of measuring a temperature for sending a signal to a remote controller or readout may be utilized without departing from the scope of the invention. In a preferred embodiment at least one sensor 66 is positioned along the esophageal lumen for measurement of the esophageal temperature above the area of the atrium 68, at least one sensor is positioned along the suction lumen 38 in the area of the atrium for measurement of the esophageal temperature within the area of the atrium and at least one sensor is positioned along the suction lumen within the area of the stomach 70 for measurement of the temperature with the stomach. The temperature sensors should generally provide an accurate measure that represents the temperature of the immediate and/or surrounding area where the sensor is positioned. The sensor should provide a signal that can be utilized for providing useful information to the controller, for example an electric signal from a thermistor. Other sensors may include fluid level sensors 72 which may be utilized to sound alarms or for operation of electromechanical valves 74 for automatic addition of cooling fluid from a remote reservoir 76. Additionally, the sensors 66 may be utilized to automatically control the flow, e.g. volumetric and start/stop, of cooling fluid using electromechanical flow control valves 60 and the like that are in electrical communication with the controller. Such valves are readily available and may include means for manual operation in addition to the electrical operation. The controller may also receive fluid from liquid detecting sensors which can be used to regulate the vacuum applied and maintained in the system. In this manner, cooling fluid would only be evacuated after a predetermined accumulation thereof.

Referring to FIGS. 1-3, the method for utilizing the esophageal cooling system includes:

providing an esophageal catheter having a phoximal balloon, wherein the phoximal balloon includes a coolant lumen therethrough for transfer of a liquid coolant, the coolant lumen terminating in a nozzle, the esophageal catheter also including a suction lumen also extending through the phoximal balloon;

a. positioning the esophageal catheter within a patients esophagus so that the phoximal balloon is positioned above the area of said patient's atria and the suction lumen extends to an area below the patient's atria;

b. occluding an upper portion of the esophagus with the phoximal balloon;

c. directing a flow of liquid coolant through the coolant lumen whereby the fluid exits the nozzle and is directed against the inner surface of the esophageal lumen;

d. evacuating the liquid coolant through the suction lumen.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification.

One skilled in the art will readily appreciate that the present invention is well adapted to carry out the objects and obtain the ends and advantages mentioned, as well as those inherent therein. Any compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An esophageal cooling system for Ablation Procedures Associated with the Cardiac Arrhythmias comprising:

an esophageal catheter including a phoximal balloon constructed and arranged for occluding an upper portion of an esophagus, said phoximal balloon including a coolant lumen therethrough for transfer of a liquid coolant, said coolant lumen terminating in a nozzle, said nozzle adapted to direct a liquid coolant against the inner surface of the esophageal lumen, said nozzle is constructed and arranged to produce a frusta-conically shaped spray of said liquid coolant, a suction lumen also extending through said phoximal balloon for evacuation of said liquid coolant, said suction lumen including at least one stand-off, said at least one stand-off constructed and arranged to extend between said suction lumen and said coolant lumen for locating and supporting said suction lumen within said central portion of said coolant lumen, said nozzle including a deflector member extending around said suction lumen for deflecting said liquid into said frusta-conically shaped spray.

2. The esophageal cooling system of claim 1 including a coolant tank, said coolant tank for containing said liquid coolant, an outlet aperture of said coolant tank in fluid communication with said coolant lumen and an inlet aperture in fluid communication with said suction lumen.

3. The esophageal cooling system of claim 2 including a coolant pump for transferring fluid from said coolant tank to said coolant lumen.

4. The esophageal cooling system of claim 3 including a flow control valve, said flow control valve constructed and arranged to control the volumetric flow of said liquid coolant flowing through said coolant lumen.

5. The esophageal cooling system of claim 2 including a vacuum pump for transferring fluid from said suction lumen to said coolant tank.

6. The esophageal cooling system of claim 2 wherein said coolant tank includes a heat exchanger constructed and arranged to maintain said liquid coolant at an operator determined temperature.

7. The esophageal cooling system of claim 2 including a controller, said controller constructed and arranged to control at least one parameter selected from the group consisting of cooling fluid flow, cooling fluid temperature, vacuum operation, vacuum pressure, and cooling fluid level within the coolant tank.

8. The esophageal cooling system of claim 2 including a controller, said controller constructed and arranged for operator control of the temperature of said cooling fluid entering said coolant lumen.

9. The esophageal cooling system of claim 8 wherein said controller is constructed and arranged for controlling the volumetric flow of said coolant liquid entering said coolant lumen, whereby said controller cooperates with an electrically operated flow control valve for controlling said volumetric flow.

10. The esophageal cooling system of claim 9 wherein said controller is constructed and arranged for controlling the vacuum pressure applied to said suction lumen.

11. The esophageal cooling system of claim 8 wherein said controller is constructed and arranged for controlling the volume of said cooling fluid within said coolant tank, whereby said controller cooperates with an electrically operated valve for allowing coolant liquid to flow into said coolant tank.

12. The esophageal cooling system of claim 1 wherein said suction lumen includes a second balloon, said second balloon positioned at a lower position of said esophagus and constructed and arranged for occluding said esophagus at a position above the stomach, said suction lumen including at least one suction port positioned above said second balloon for transfer of said liquid cooling fluid to the inside of said suction lumen.

13. The esophageal cooling system of claim 1 including a second suction lumen, said second suction lumen positioned above said phoximal balloon for removing accumulated liquids above said phoximal balloon.

14. The esophageal cooling system of claim 1 wherein at least one of said phoximal balloon, said coolant lumen and said suction lumen include at least one marker band constructed from a radio-opaque material.

15. The esophageal cooling system of claim 1 wherein at least one of said phoximal balloon, said coolant lumen and said suction lumen include a thermister.

16. The esophageal cooling system of claim 15 wherein said thermister is in electrical communication with a controller.

17. A method of cooling an esophagus for Ablation Procedures Associated with the Left Atrium comprising:
- providing an esophageal catheter having a phoximal balloon, said phoximal balloon including a coolant lumen therethrough for transfer of a liquid coolant, said coolant lumen terminating in a nozzle, said nozzle is constructed and arranged to produce a frusta-conically shaped spray of said liquid coolant, said esophageal catheter also including a suction lumen also extending through said phoximal balloon, said suction lumen including at least one stand-off, said at least one stand-off constructed and arranged to extend between said suction lumen and said coolant lumen for locating and supporting said suction lumen within said central portion of said coolant lumen, said nozzle including a deflector member extending around said suction lumen for deflecting said liquid into said frusta-conically shaped spray;
- positioning said esophageal catheter within a patient's esophagus so that said phoximal balloon is positioned above the area of said patient's atria and said suction lumen extends to an area below said patient's atria;
- occluding an upper portion of said esophagus with said phoximal balloon;
- directing a flow of liquid coolant through said coolant lumen whereby said fluid exits said nozzle and is directed against the inner surface of the esophageal lumen;
- evacuating said liquid coolant through said suction lumen.

\* \* \* \* \*